US006402829B1

(12) United States Patent
Sung et al.

(10) Patent No.: US 6,402,829 B1
(45) Date of Patent: Jun. 11, 2002

(54) PROCESS FOR PREPARING A SUBSTANTIALLY PURE GAMMA PHASE QUINACRIDONE PIGMENT OF LARGE PARTICLE SIZE

(75) Inventors: Edward H. Sung, Cincinnati; George H. Robertson, Loveland; Humberto Velasquez, Cincinnati, all of OH (US)

(73) Assignee: Sun Chemical Corporation, Fort Lee, NJ (US)

( * ) Notice: Subject to any disclaimer, the term of this patent is extended or adjusted under 35 U.S.C. 154(b) by 0 days.

(21) Appl. No.: 09/741,389

(22) Filed: Dec. 20, 2000

(51) Int. Cl.[7] ................................................ C09B 48/00
(52) U.S. Cl. ...................... 106/497; 106/31.77; 546/49; 546/56
(58) Field of Search ................................ 106/493, 497, 106/31.77; 546/49, 56

(56) References Cited

U.S. PATENT DOCUMENTS

| 3,256,285 A | | 6/1966 | Fuchs et al. ................. 260/279 |
| 3,579,519 A | | 5/1971 | Schweizer ................... 260/279 |
| 4,099,980 A | * | 7/1978 | North ........................ 106/495 |
| 4,197,404 A | * | 4/1980 | Johnson ...................... 106/497 |
| 4,212,975 A | | 7/1980 | Kroh et al. .................. 546/49 |
| 4,247,696 A | | 1/1981 | Shibata et al. ................ 546/49 |
| 4,758,665 A | | 7/1988 | Spietschka et al. ............ 546/49 |
| 4,760,144 A | * | 7/1988 | Jaffe .......................... 106/497 |
| 4,895,948 A | | 1/1990 | Jaffe et al. .................... 546/56 |
| 5,084,573 A | | 1/1992 | Babler et al. ................. 546/56 |
| 5,095,056 A | | 3/1992 | Babler et al. ................. 524/90 |
| 5,223,624 A | * | 6/1993 | Babler et al. ................ 106/497 |
| 5,383,966 A | | 1/1995 | Johnson ...................... 106/495 |
| 5,755,872 A | * | 5/1998 | Urban et al. ................. 106/493 |
| 6,139,822 A | | 10/2000 | Socci et al. .................. 424/61 |
| 6,312,512 B1 | * | 11/2001 | Urban et al. ............... 106/31.77 |
| 6,323,342 B1 | * | 11/2001 | Babler ........................ 106/497 |

FOREIGN PATENT DOCUMENTS

| GB | 828052 | 7/1956 | |
| GB | 1080394 | 7/1966 | ........... C09B/57/00 |
| JP | 39-20073 | 9/1964 | |
| JP | 59-122550 | * 7/1994 | |
| JP | 59-122551 | * 7/1994 | |

* cited by examiner

*Primary Examiner*—Anthony Green
(74) *Attorney, Agent, or Firm*—Sidney Persley

(57) ABSTRACT

An improved process for producing a substantially pure gamma phase a quinacridone pigment or pigment derivative involving preparing an aqueous slurry of a crude quinacridone in the presence of caustic alkali and a non-polar, water immiscible solvent; and heating said slurry at a temperature above about 120° C.

10 Claims, No Drawings

PROCESS FOR PREPARING A SUBSTANTIALLY PURE GAMMA PHASE QUINACRIDONE PIGMENT OF LARGE PARTICLE SIZE

FIELD OF THE INVENTION

The present invention relates to a conditioning process for quinacridone pigment and quinacridone derivatives, useful as colorants for printing inks. More particularly, the invention relates to treatment of quinacridone and quinacridone derivatives at elevated temperatures with caustic alkali and non-polar water immiscible solvent to produce a substantially pure gamma phase quinacridone pigment of large particle size.

BACKGROUND OF THE INVENTION

It is well known that opaque quinacridones of gamma phase with a high covering power can be prepared from two different approaches. One approach requires milling the large particle quinacridone crude with salt or conditioning the extremely fine quinacridone crude in solvent. For example, the cyclization of 2,5-dianilino-3,6-dihydro terephthalic acid or its methyl ester in Dowthern A (available from Dow Chemical Co., Midland, Mich.) will generate 6,13-dihydroquinacridone of large particle size. Oxidation of 6,13-dihydroquinacridone in aqueous methanol in the presence of sodium hydroxide yields a crude quinacridone which is subjected to salt-milling. Quinacridone of gamma modification is then produced by either treating the salt-milled material with various organic solvents or milling the crude with inorganic salt in the presence of an alcohol and a base.

In another approach, quinacridone crude can be prepared by cyclizing 2,5-dianilinoterephthalic acid in strong acid, e.g., polyphosphoric acid or its acid methyl ester. The resulting crude is extremely small and requires after-treatment to increase particle size for arbitrary application.

Crude quinacridones are normally conditioned with organic solvents to give dispersible pigments. For example, U.S. Pat. No. 4,895,948 discloses a one-step finishing process in which a crude quinacridone is ball milled in an alcohol containing a base. U.S. Pat. No. 5,084,573 also discloses a one-step finishing process in which 2,9-dichloroquinacridone is stirred in heated polar organic solvents containing, as essential ingredients, cedain long-chain thiol compounds and a base. U.S. Pat. No. 5,095,056 discloses a process for conditioning 2,9-dichloroquinacridone using large quantities of polar solvents, including esters such as methyl benzoate, at temperatures above 50° C. Although bases and other such additional compounds are not required, the polar solvent is used in an amount that is about 3 to 20 times the weight of the pigment. Water can be tolerated but is not preferred. U.S. Pat. No. 3,256,285 similarly discloses a process for finishing aqueous pastes of quinacridones in large quantities of organic solvent (4 to 10 times the amount of pigment) at temperatures of 80° to 150° C. When using high-boiling or water-immiscible solvents (such as methyl benzoate and methyl salicylate) according to U.S. Pat. No. 3,256,285, the presscake must be washed with low boiling organic solvents, thus requiring the disposal of significant quantities of organic liquids which is more costly and time consuming.

U.S. Pat. No. 5,383,966 describes the preparation of quinacridone in methyl benzoate and aromatic esters (as the polar organic solvent) in relatively small quantities and without the need for special additives. However, the suitable quinacridone for this method is specified as 2,9-dimethylquinacridone, 2,9-dicholoquinacridone or solid solution of either chemical with unsubstituted quinacridone. Furthermore, it is important to note that caustic alkali is not used during the conditioning step in this method but rather is added after conditioning to hydrolyze methyl benzoate. The solvent used is methyl benzoate which is a polar solvent.

The present invention provides an improved and economic method for preparing gamma phase quinacridone of large particle size using caustic alkali and a non-polar water immiscible solvent.

SUMMARY OF THE INVENTION

The present is an improved process for conditioning a quinacridone pigment and quinacridone derivatives comprising: (a) preparing an aqueous slurry of a crude quinacridone in the presence of caustic alkali and a non-polar, water immiscible solvent; and (b) heating said slurry at a temperature above about 120° C. thereby producing a substantially pure gamma phase quinacridone pigment.

DETAILED DESCRIPTION OF THE INVENTION

It has been surprisingly found that substantially pure gamma crystal phase quinacridone pigment or derivative of large particle size can be prepared by treating a crude quinacridone preparation with water and caustic alkali in the presence of small amount of non-polar, water immiscible, solvent at a temperature above about 120° C., and more preferably from about 120° C. to about 170° C., to give a soft and opaque pigment. The addition of caustic alkali and non-polar, water immiscible solvent is essential to the success of this invention. Elimination of caustic from process prevents the complete conversion of the alpha crude into the gamma modification and the removal of solvent retards crystal conversion totally.

The crude quinacridone can be prepared in a number of ways. Preferably, crude quinacridone is prepared by: (a) dissolving 2,5-dianilinoterephthalic acid in polyphosphoric acid (PPA), at a temperature of about 90 to 130° C. to result in a magma; and (b) striking the resulting mixture (i.e. magma) into water to precipitate alpha phase crude quinacridone.

While dissolving 2,5-dianilinoterephthalic acid in PPA, the concentration and temperature of PPA are key elements affecting product opacity and cleanness. A high PPA concentration and low condensation temperature generally results in a crude which can be opacified easier. The PPA concentration can be increased through the addition of $P_2O_5$. It is preferable to maintain the PPA concentration between 117% to 119% and to control the condensation temperature at 90 to 120° C. A lower PPA concentration or higher condensation temperature will result in a dark and poor dispersible pigment. After cyclization of 2,5-dianilinoterephthalic acid, the PPA mixture is then poured into water to precipitate quinacridone crude.

Preferably, the resulting crude quinacridone is washed to conductivity below 1000 mu, more preferably below 800 mu.

The purity of the 2,5-dianilinoterephthalic acid intermediate often affects product quality and therefore must be kept as high as possible. Major impurities such as 2-anilinoterephthalic acid and 2,5-dianilinobenzoic acid should be eliminated or substantially reduced during the preparation of intermediate. To maintain consistent quality of final pigment, the purity of 2,5-dianilinoterephthalic acid is preferably 98.0% or higher.

The crude quinacridone, which is in the form of alpha phase, may be washed thoroughly with water before reslurrying back into water. The filtercake must be broken down entirely to form a good dispersion. Any undispersible lump will lead to a dark, dirty and bluish material. The amount of water used should be enough to provide a fluidable mass and is preferable 10 to 15 times the pigment weight. Frequently, small amounts of surfactant can be added to the slurry to improve dispersion.

Both organic and inorganic alkali may be used in the conditioning process, but the caustic alkali such as sodium hydroxide, potassium hydroxide or lithium hydroxide is preferred due to their low cost. The alkali increases the ionic characteristics of quinacridone and speeds up particle size growth in water. The amount of caustic alkali is preferable at 0.3 to 0.8 times of pigment weight. Shortage of caustic would slow down the opacification process and result in a dark and dull pigment. Elimination of caustic from process prevents the complete conversion of alpha crystal into gamma modification, in certain case, such as at elevated temperature, part of alpha crystal can even transform into beta crystal.

Various types of non-polar, water immiscible solvent, such as xylene, alpha-olefin, textile spirits, mineral spirits and many aliphatic hydrocarbon solvents can be applied in this invention. Due to its water immiscible nature, it often encapsulates pigment and forms bead-like particles. The physical condition of the encapsulated pigment facilitates not only filtration speed but also provides soft texture after drying. The amount of non-polar solvent is preferable at about 0.1 to 2 part of pigment weight. Raising the amount of solvent will not affect the pigment quality but simply increasing the cost of production. However, the elimination of solvent from this process would be detrimental to the product in which the crude is unable to convert into gamma modification and results in a dark and dull material.

The pigment slurry after addition of solvent is heated slowly to a high temperature above 120° C. The suitable temperature is around 130–160° C. and is preferable at 140–150° C. The length of heating is depended on the level of temperature and generally higher temperature requires less time to achieve similar particle size. The mixture is then cooled to 60° C. before filtration and the presscake is washed to alkali free and dried to give an opaque, easy dispersible quinacridone with gamma modification.

Pigment made from this invention possesses a cherryish red with good covering power and its excellent light-fastness and heat stability are of considerable industrial importance for pigmenting finishes and paints and for coloring plastics.

Because of their light stability and migration properties, the quinacridone pigments prepared according to the present invention are suitable for many different pigment applications. For example, pigments prepared according to the invention can be used as the colorant (or as one of two or more colorants) for very light-fast pigmented systems. Examples include pigmented mixtures with other materials, pigment formulations, paints, printing ink, colored paper, or colored macromolecular materials. The term "mixtures with other materials" is understood to include, for example, mixtures with inorganic white pigments, such as titanium dioxide (rutile) or cement, or other inorganic pigments. Examples of pigment formulations include flushed pastes with organic liquids or pastes and dispersions with water, dispersants, and, if appropriate, preservatives. Examples of paints in which pigments of this invention can be used include, for example, physically or oxidatively drying lacquers, stoving enamels, reactive paints, two-component paints, solvent- or water-based paints, emulsion paints for weatherproof coatings, and distempers. Printing inks include those known for use in paper, textile, and tinplate printing. Suitable macromolecular substances include those of a natural origin, such as rubber; those obtained by chemical modification, such as acetyl cellulose, cellulose butyrate, or viscose; or those produced synthetically, such as polymers, polyaddition products, and polycondensates. Examples of synthetically produced macromolecular substances include plastic materials, such as polyvinyl chloride, polyvinyl acetate, and polyvinyl propionate; polyolefins, such as polethylene and polypropylene; high molecular weight polyamides; polymers and copolymers of acrylates, methacrylates, acrylonitrile, acrylamide, butadiene, or styrene; polyurethanes; and polycarbonates. The materials pigmented with the quinacridone pigments of the present invention can have any desired shape or form.

The pigments prepared according to this invention are highly water-resistant, oil-resistant, acid-resistant, lime-resistant, alkali-resistant, solvent-resistant, fast to over-lacquering, fast to over-spraying, fast to sublimation, heat-resistant, and resistant to vulcanizing, yet give a very good tinctorial yield and are readily dispersible (for example, in plastic materials such as polyvinyl chloride and ABS).

The invention will be illustrated by the following specific examples, but it is to be understood that it is not limited to the details thereof and that changes may be made without departing from the scope of the invention.

EXAMPLE 1

Polyphosphoric acid (PPA, 913.6 g) is heated to 90° C. and 2,5-dianilinoterephthalic acid (168 g) is added to it over three hours. The PPA temperature is maintained between 90–105° C. during addition and the mixture is hold at 100–105° C. for additional half hours after addition. Twenty four grams of water is then added to mixture slowly to dilute the PPA and the temperature is maintained at 100–105° C. The diluted mixture is poured into water (3,336.00 g) at 10° C. and the resulting slurry is stirred for 3 hours to assure the complete hydrolysis. The mixture is then filtered and washed with water until free of acid.

The above presscake (30 g) is added to a Parr pressure reactor, along with water (370 g), mineral spirits (30 g), 50% sodium hydroxide (30 g) and Aerosol OT (1.5 g). The mixture is mixed thoroughly for 3 minutes and is heated slowly to 150° C. The temperature is held at 150° C. for an additional 4 hours and is cooled to 60° C. before filtration. The filtercake is then washed with water until pH is less than 9. The presscake is then dried at 80° C. and after grinding, it gives a soft, opaque pigment of gamma formation.

EXAMPLE 2

Example 1 is repeated. After addition of crude, water, mineral spirits and Aerosol OT in pressure reactor, the mixture is simply mixed with agitator without the homogenization. The pigment slurry is then heated slowly to 150° C. and the temperature is held at 150° C. for additional 4 hours. The reaction mixture is cooled to 60° C. and is filtered. The filtercake is then washed with water until pH is less than 9. The presscake is then dried at 80° C. and after grinding, it gives a product which is slightly darker, bluer and dirtier than that made from Example 1.

EXAMPLE 3

Comparative

Crude presscake (30 g, dry basis) is added to a Parr pressure reactor, along with water (370 g), 50% sodium hydroxide (30 g) and Aerosol OT (1.5 g). The mixture is mixed for 3 minutes (no mineral spirits is added) and is heated slowly to 150° C. The temperature is held at 150° C. for an additional 4 hours and is cooled to 60° C. before filtration. The filtercake is washed with water until pH is less than 9. The presscake is then dried at 80° C. and after grinding, it gives a considerable dull, dark pigment of predominate alpha formation.

EXAMPLE 4

Comparative

Crude presscake (30 g, dry basis) is added to a Parr pressure reactor, along with water (370 g), mineral spirits (30 g) and Aerosol OT (1.5 g). The mixture is mixed thoroughly for 3 minutes and is heated slowly to 150° C. The temperature is held at 150° C. for an additional 4 hours and is cooled to 60° C. before filtration. The filtercake is washed with water until pH is less than 9. The presscake is dried at 80° C. and after grinding, it gives a considerable dull, dark pigment of mix crystals which contain both gamma and alpha formation and 4 to 5% of beta formation.

The invention has been described in terms of preferred embodiments thereof, but is more broadly applicable as will be understood by those skilled in the art. The scope of the invention is only limited by the following claims.

What is claimed is:

1. A process for conditioning a quinacridone pigment or pigment derivative comprising:
    (a) preparing an aqueous slurry of a crude quinacridone in the presence of caustic alkali and a non-polar, water immiscible solvent; and
    (b) heating said slurry at a temperature above about 120° C. resulting in a substantially pure gamma phase quinacridone pigment of large particle size.

2. The process of claim 1 wherein the caustic alkali is selected from the group consisting of sodium hydroxide, potassium hydroxide and lithium hydroxide.

3. The process of claim 1 wherein the caustic alkali is sodium hydroxide.

4. The process of claim 1 wherein the non-polar water immiscible solvent is selected from the group consisting of mineral spirits, xylene and alpha-olefins.

5. The process of claim 4 wherein the non-polar water immiscible solvent is mineral spirits.

6. The process of claim 1 wherein said heating is carried out at a temperature of about 120 to 170° C.

7. The process of claim 1 wherein the crude quinacridone is used as presscake containing 4 to 70 wt. % quinacridone pigment, with the balance being essentially water.

8. The process of claim 1 wherein the gamma phase quinacridone pigment is collected from said slurry by filtration after the heating step.

9. A quinacridone pigment conditioned by the process of claim 1.

10. A printing ink comprising a quinacridone pigment conditioned by the process of claim 1.

* * * * *

UNITED STATES PATENT AND TRADEMARK OFFICE
CERTIFICATE OF CORRECTION

PATENT NO.    : 6,402,829 B1
DATED         : June 11, 2002
INVENTOR(S)   : Sung et al.

It is certified that error appears in the above-identified patent and that said Letters Patent is hereby corrected as shown below:

<u>Column 1,</u>
Line 9, "as colorants for printing inks" should be amended to read -- as colorants for printing inks, coatings and plastics --.

Signed and Sealed this

Fourth Day of February, 2003

JAMES E. ROGAN
*Director of the United States Patent and Trademark Office*